(12) United States Patent
Aletto et al.

(10) Patent No.: US 8,389,838 B2
(45) Date of Patent: Mar. 5, 2013

(54) GUITAR PICK HOLDER ORNAMENT

(75) Inventors: Mark V. Aletto, Moon Township, PA (US); Richard J. Mackey, Moon Township, PA (US)

(73) Assignee: Impressive Impressions, Inc., Moon Township, PA (US)

( * ) Notice: Subject to any disclaimer, the term of this patent is extended or adjusted under 35 U.S.C. 154(b) by 0 days.

(21) Appl. No.: 12/681,214

(22) PCT Filed: Oct. 6, 2008

(86) PCT No.: PCT/US2008/078897
§ 371 (c)(1),
(2), (4) Date: Apr. 1, 2010

(87) PCT Pub. No.: WO2009/046401
PCT Pub. Date: Apr. 9, 2009

(65) Prior Publication Data
US 2010/0206154 A1 Aug. 19, 2010

Related U.S. Application Data

(60) Provisional application No. 60/977,973, filed on Oct. 5, 2007.

(51) Int. Cl.
*G10D 3/16* (2006.01)

(52) U.S. Cl. ......................................................... 84/320
(58) Field of Classification Search ............. 84/320–322
See application file for complete search history.

(56) References Cited

U.S. PATENT DOCUMENTS

| | | | |
|---|---|---|---|
| 5,905,217 | A | 5/1999 | Byers |
| 5,950,287 | A | 9/1999 | Cacciatore et al. |
| D561,237 | S | 2/2008 | Morris |
| D577,379 | S | 9/2008 | Morris |
| D584,984 | S | 1/2009 | Morris |
| 7,626,103 | B1 * | 12/2009 | Phillips ........................... 84/320 |
| 2005/0045020 | A1 * | 3/2005 | Pittman et al. .................. 84/322 |
| 2005/0092158 | A1 * | 5/2005 | Santa Cruz et al. ............. 84/322 |
| 2007/0151315 | A1 | 7/2007 | Vincent |
| 2008/0110319 | A1 | 5/2008 | Morris |
| 2009/0249831 | A1 * | 10/2009 | Morris ........................... 63/1.12 |

FOREIGN PATENT DOCUMENTS

WO 2006046918 A1 5/2006

* cited by examiner

*Primary Examiner* — Kimberly Lockett
(74) *Attorney, Agent, or Firm* — McNees Wallace & Nurick LLC

(57) ABSTRACT

A guitar pick holder with a recessed rim and a rear support plate for receiving and securing guitar picks. A fastener or a hoop for accepting a material provides means for the guitar pick to be ornamentation. An opening in the holder allows visibility to the guitar pick when the guitar pick is placed in the holder ornament.

15 Claims, 10 Drawing Sheets

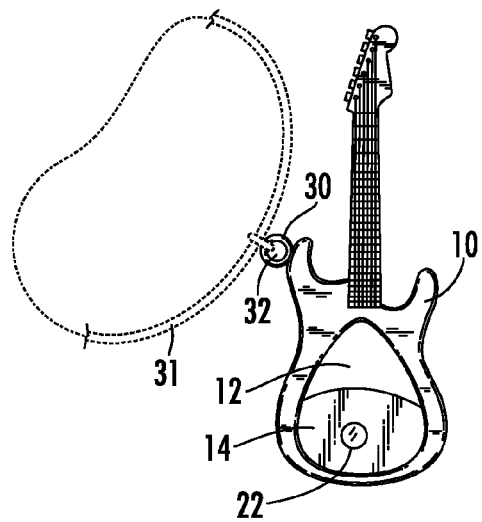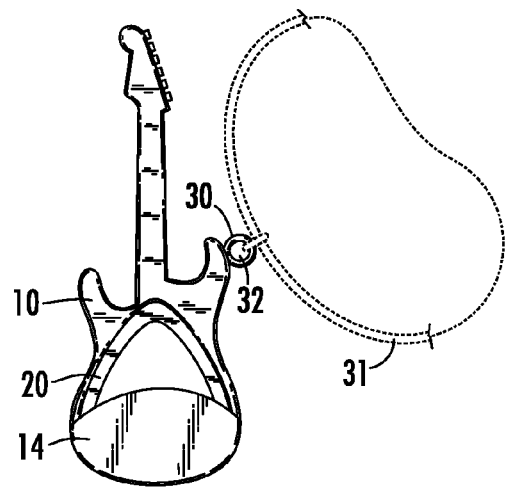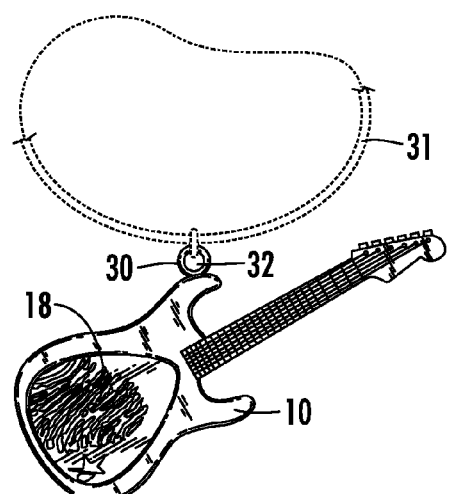

GUITAR PICK HOLDER ORNAMENT

CROSS REFERENCE TO RELATED PATENT APPLICATIONS

This application claims priority to U.S. Provisional Patent Application No. 60/977,673, filed on Oct. 5, 2007, whose disclosure is incorporated by reference in its entirety into this application.

BACKGROUND OF THE INVENTION

The present invention is directed to a guitar pick holder, and more specifically to a guitar pick holder that is also an ornament.

A guitar is typically played with a "guitar pick", which is used to strike or pluck strings of the guitar. Many guitar players carry a number of guitar picks with them as they are relatively small, easily lost, and inexpensive. However, it is often inconvenient to store or retrieve guitar picks. Guitar picks are typically carried in pants pockets and/or within guitar cases and need to be retrieved when the guitar is played. When a guitar is taken out of its guitar case, for example, a guitar pick must be retrieved from some location. Conversely, when a guitar is placed back in its case, the guitar pick must be stored somewhere. When a guitar player is playing and accidentally drops or intentionally tosses away the guitar pick, it is desirable to be able to quickly retrieve another one.

The appearance of guitars and guitar picks are also important to guitar players, and therefore it is preferable that any method used to hold or carry guitar picks does not detract from how these items look. Furthermore, any guitar pick holding system should be inexpensively made so that it may become commercially available and ubiquitous to a large number of consumers. Promotional techniques are also important in the industry.

Prior art describes a magnetic solution for holding guitar picks, where a flexible magnet is adhered to a guitar and the guitar picks include a metal material. The flexible magnet may include a rear static cling vinyl adhering surface for adhering to a glossy surface of a guitar. In addition a laminate of static cling vinyl and polyester is used for the same purpose.

Another form of prior art describes a guitar pick formed from a blend of plastic and metal material to have the look-and-feel of a plastic guitar pick but still be magnetically attractable. In yet another form of prior art, a guitar pick sticker which is used to adhere to a surface of a guitar pick to make it magnetically attractable so that it can be used with a magnetic guitar pick holder. Even though such guitar pick holding solutions are available, in some cases it may not be preferred to use special guitar picks or to modify off-the-shelf guitar picks. In addition, these methods and systems all include holding the guitar pick on the front of the guitar. In some cases, it may not be preferred to use a guitar pick holder that modifies the aesthetics of the guitar.

Therefore, what is needed is a guitar pick holder that allows the user to have quick access to the pick, but not affect the aesthetics of the guitar. It also needed to have a guitar pick holder that protects the guitar pick. It is further needed to have a guitar pick holder that is a novelty in the form of unisex ornamentation, such as, but not limited to jewelry or costume jewelry.

SUMMARY OF THE INVENTION

One embodiment is directed to a guitar pick holder ornament having a frame with a recessed rim configured to receive at least one guitar pick. The guitar pick holder also includes a support plate secured to the frame. The support plate secures the at least one guitar pick in the recessed rim of the frame.

Another embodiment is directed to a guitar pick holder including a frame having body, and at least one clasp extending from the body. The at least one clasp curves adjacent and substantially parallel to the body. At least one guitar pick is placed in the frame and the at least one clasp secures the at least one guitar pick in the frame.

Yet another embodiment is directed to a guitar pick holder having a frame. The frame includes a first half with a recessed rim configured to receive a guitar pick. The frame also includes a second half with a recessed rim configured to receive a guitar pick. The second frame attaches to the first frame in at least an open position and a closed position. The guitar pick is secured in the guitar pick holder when the first frame and second frame are in the closed position.

One advantage of the present invention includes having an easily accessible guitar pick that does not impact the guitar frame.

Another advantage of the present invention is that the guitar pick holder is applicable for any size and gauge of guitar pick.

Another advantage is the ability to display the guitar pick as part of an ornament without altering the pick.

Yet another advantage is that the present invention preserves the future collectable value of the guitar pick.

Still another advantage of the present invention is that it may be used as an ornament, a golf ball marker, a poker chip holder, or a display for coins.

Another advantage of the present invention is that both sides of the guitar pick may be visible when placed in the frame.

Yet another advantage of the present invention is that the design allows for full display of the pick without altering the pick in any manner.

Still another advantage of the present invention is that it may be used to carry multiple or spare guitar picks.

Other features and advantages of the present invention will be apparent from the following more detailed description of the preferred embodiment, taken in conjunction with the accompanying drawings which illustrate, by way of example, the principles of the invention

BRIEF DESCRIPTION OF THE DRAWINGS

FIG. 4 is a front view of another embodiment of a guitar pick holder ornament.

FIG. 5 is a rear view of the guitar pick holder ornament in FIG. 4.

FIG. 6 is a front view of the guitar pick holder ornament in FIG. 4 with a guitar pick inserted therein.

Wherever possible, the same reference numbers will be used throughout the drawings to refer to the same or like parts.

DETAILED DESCRIPTION OF THE INVENTION

Figure 1:
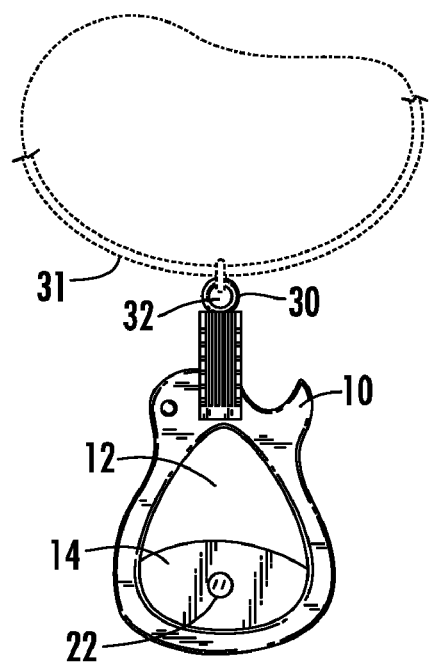
FIG. 1 is a front view of a guitar pick holder ornament.
Figure 2:
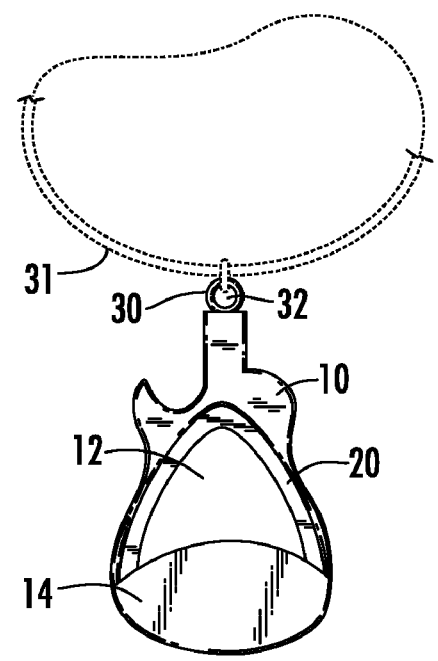
FIG. 2 is a rear view of the guitar pick holder ornament in FIG. 1.
Figure 3:
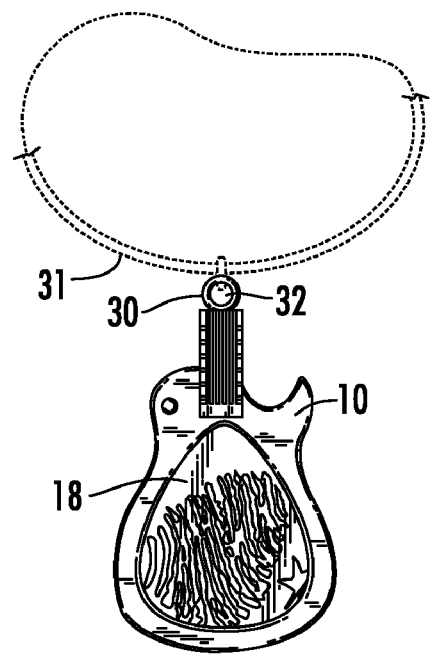
FIG. 3 is a front view of a guitar pick holder ornament in FIG. 1 with a guitar pick inserted therein.

Referring to FIGS. 1 through 3, one embodiment of a guitar pick frame 10 has an opening 12 that is shaped with a configuration to expose a standard sized guitar pick 18. Frame 10 also includes a recessed rim 20 for accepting guitar pick 18. Recessed rim 20 generally has a smaller diameter than opening 12, such that the rim of recessed rim 20 supports guitar pick 18 and prevents guitar pick 18 from falling through opening 12. The depth of recessed rim 20 is such that when guitar pick 18 is placed in recessed rim 20, guitar pick 20 is substantially flush with frame 10. The diameter configuration of recessed rim 20 typically matches the shape of guitar pick 18, such that when guitar pick 18 is placed in frame 10, guitar pick 18 rests securely in recessed rim 20 with substantially no excess space between the edges of recessed rim 20 and the edges of guitar pick 18.

Frame 10 is a continuous structure that is designed to encompass the edges of guitar pick 18 when guitar pick 18 is inserted into frame 10. While guitar pick 18 is available in many shapes, gauges and sizes, there exists a standard shape and size for guitar pick 18 of a generally triangular configuration, generally having rounded corners. Thus, recessed rim 20 and opening 12 have a triangular shaped configuration with rounded corners 16. Other shapes of a guitar pick 18 may include a teardrop shape, heart shape, or any other suitable shape. Thus, opening 12 and recessed rim 20 may be configured to accept a teardrop shape, heart shape, or any other suitable shaped guitar pick 18. Opening 12 may have other non-triangular shapes and still expose guitar pick 18. For example, opening 12 may have a heart shape, circular shape, square shape, or any other suitable desired shape and provide exposure to guitar pick 18, while recessed rim 20 has a suitable shape for securing guitar pick 18.

A rear support plate 14 is disposed and secured to one side of frame 10 to secure guitar pick 18 in frame 10. Rear support plate has a substantially flat surface and substantially covers a portion, e.g., approximately one third of opening 12, to support pick 18 when pick 18 is placed in frame 10. Support plate, or rear support plate 14 may be integral with frame 10, or rear support plate 14 may be a separate piece secured to frame 10 with an adhesive or other suitable bond, connection, hinge, or fastening means. As shown in FIGS. 1 through 3, rear support plate 14 has rounded edges, however it should be known that any type of edge configuration may be used for rear support plate 14, such as straight, pointed, wavy, etc. Rear support plate 14 is also shown as being disposed at the bottom of frame 10, however rear support plate 14 may be placed at any location of frame 10. Guitar pick 18 is placed in frame 10 such that guitar pick 18 is disposed in recessed rim 20 between frame 10 and rear support plate 14 with recessed rim 20 preventing guitar pick 18 from falling out of frame 10 on one side and with rear support plate 14 preventing guitar pick 18 from falling out of frame 10 on the other side.

A cushion 22 may be disposed on rear support plate 14 to press guitar pick 18 firmly against recessed rim 20. Cushion 22 compensates for any space between pick 18 and rear support plate 14 when pick 18 is placed in frame 10. Guitar picks 18 are available in various thicknesses, thus frame 10 typically includes a thickness suitable to accommodate picks 18 of different thicknesses. Cushion 22 is shown as covering only a portion of rear support plate 14, however cushion 22 may substantially cover rear support plate 14, or a larger portion of rear support plate 14 than shown.

Guitar pick 18 is inserted into frame 10 by inserting a portion of guitar pick through opening 12 between recessed rim 20 and rear support plate 14. Guitar pick 18 is inserted fully until guitar pick 18 is secured firmly into recessed rim 20 and cushion 22 is compressed against guitar pick 18. Once guitar pick 18 is placed in frame 10, pick 18 is not removable unless a force is applied to guitar pick 18. Guitar pick 18 is not easily movable from frame 10 with basic movements or light forces associated with normal wear of ornaments. Pick 18 is removed from frame 10 by flexing pick 18 against rear support plate 14 and removing guitar pick 18 from recessed rim 20.

Frame 10 also includes a hoop 30 having an aperture 32 for receiving an ornamental material 31 to create an ornament. For example, a chain of suitable gauge and length may be strung through aperture 32 to create a necklace having frame 10 as a pendant. Further, any suitable ornamental material may be used to create ornaments such as, but not limited to an earring, a bracelet, an anklet, a belly ring, a keychain, a zipper pull, a luggage tag, and/or a ring. Hoop 30 may be integral with frame 10, or hoop 30 may be secured, adhered, fastened, or otherwise connected to frame 10. Hoop 30 may also be secured to frame 10 at the top of frame 10, however hoop 30 may be secured to frame 10 at any suitable location. Frame 10 may also include a fastener (not shown) for securing frame 10 to a device such as, but not limited to a guitar, belt loop, shirt, pants, cell phone, shoe or other suitable device.

Figure 7:
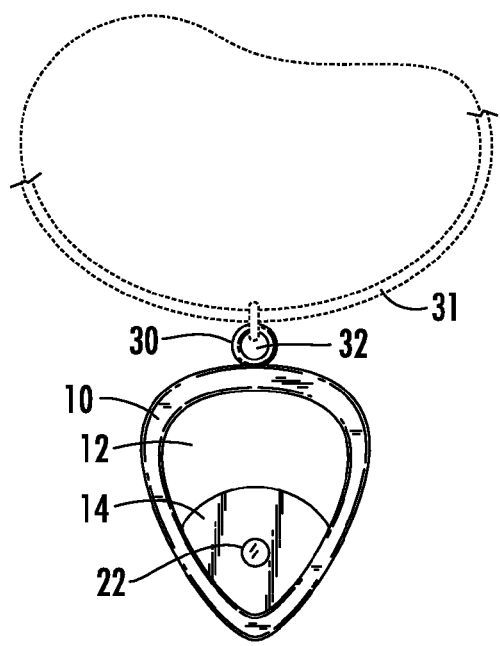
FIG. 7 is a front view of yet another embodiment of a guitar pick holder ornament.
Figure 8:
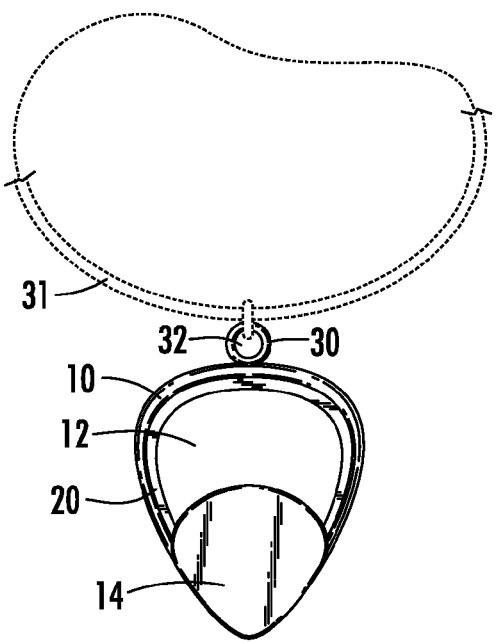
FIG. 8 is a rear view of the guitar pick holder ornament in FIG. 7.
Figure 9:
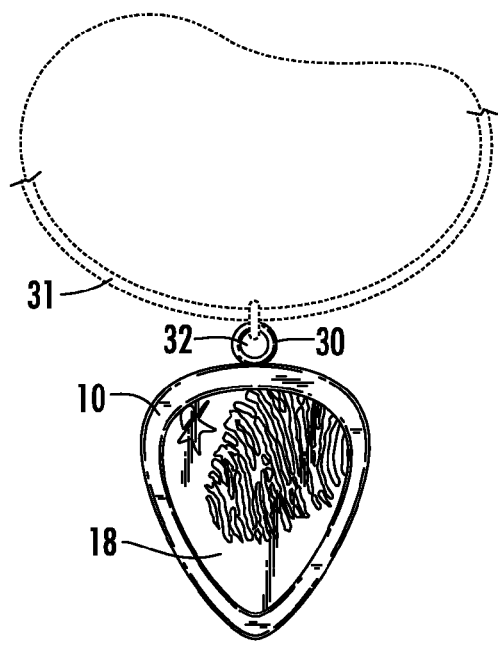
FIG. 9 is a front view of the guitar pick holder ornament in FIG. 7 with a guitar pick inserted therein.
Figure 10:
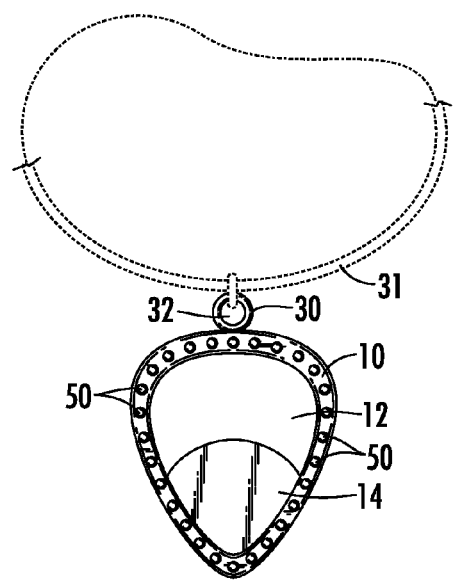
FIG. 10 is a front view of still another embodiment of a guitar pick holder ornament.
Figure 11:
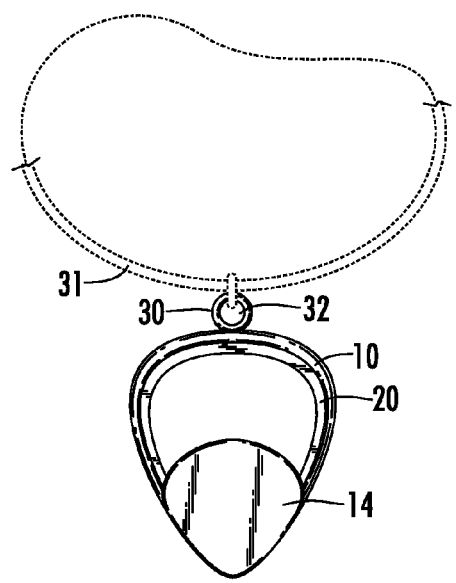
FIG. 11 is a rear view of the guitar pick holder ornament in FIG. 10.
Figure 12:
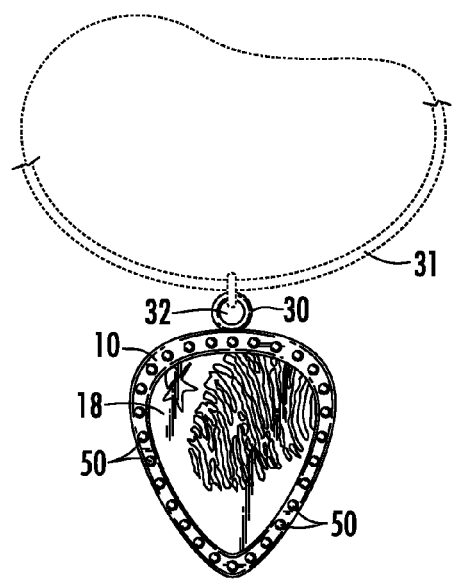
FIG. 12 is a front view of the guitar pick holder ornament in FIG. 10 with a guitar pick inserted therein.
Figure 13:
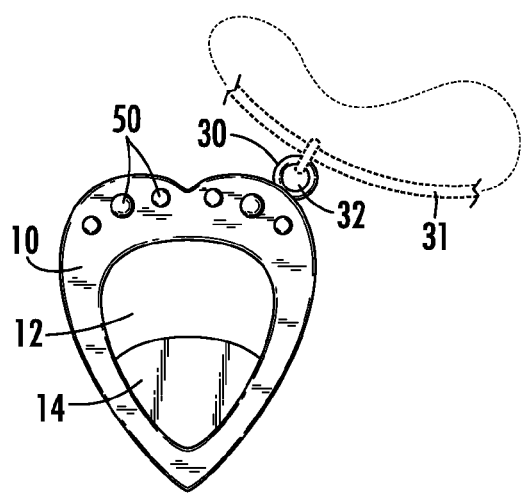
FIG. 13 is a front view of another embodiment of a guitar pick holder ornament.
Figure 14:
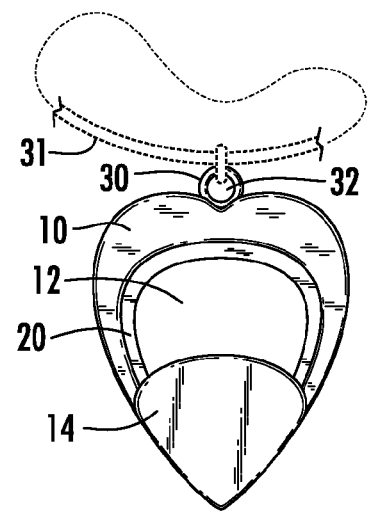
FIG. 14 is a rear view of the guitar pick holder ornament in FIG. 13.
Figure 15:
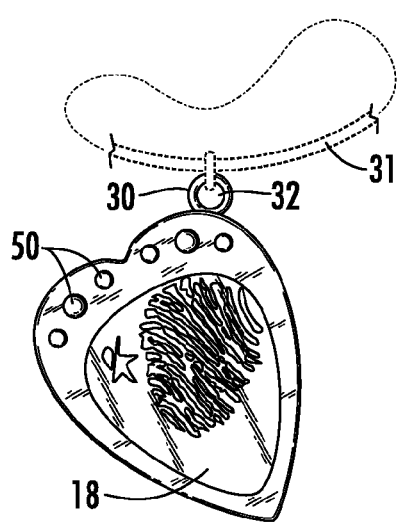
FIG. 15 is a front view of the guitar pick holder ornament in FIG. 13 with a guitar pick inserted therein.
Figure 16:
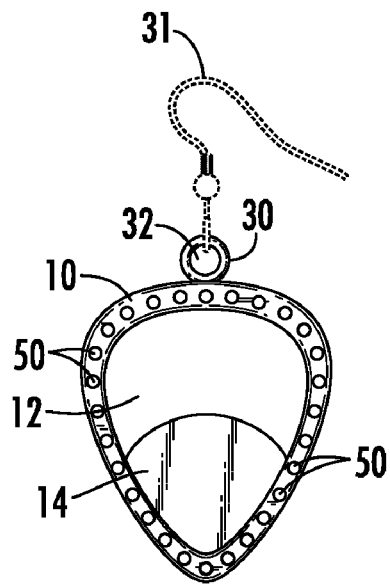
FIG. 16 is a front view of yet another embodiment of a guitar pick holder ornament.
Figure 17:
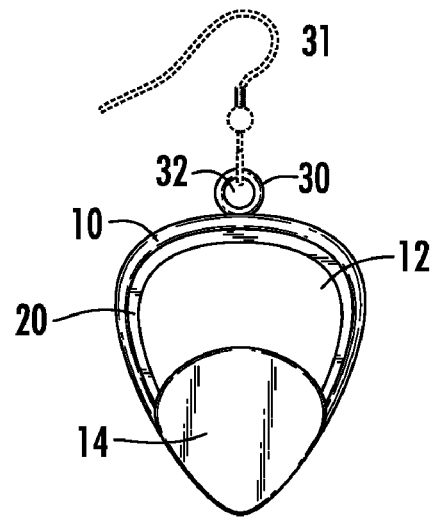
FIG. 17 is a rear view of the guitar pick holder ornament in FIG. 16.
Figure 18:
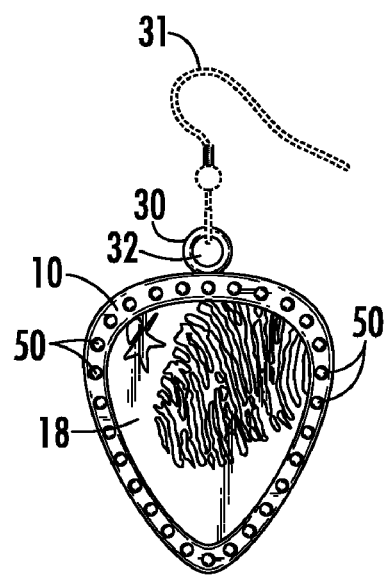
FIG. 18 is a front view of the guitar pick holder ornament in FIG. 16 with a guitar pick inserted therein.
Figure 19:
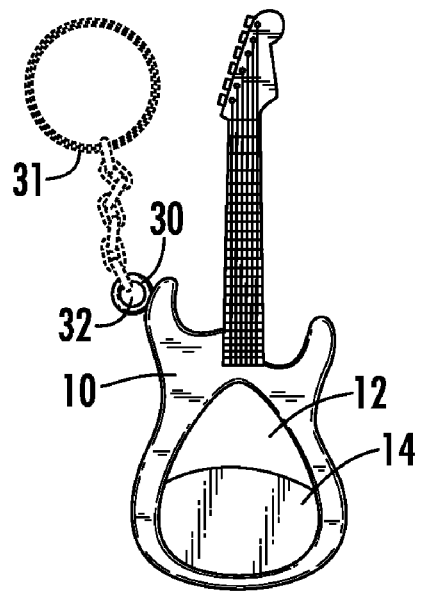
FIG. 19 is a front view of still another embodiment of a guitar pick holder ornament.
Figure 20:
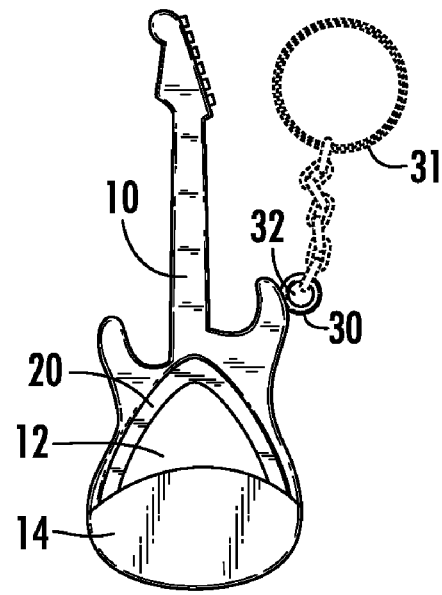
FIG. 20 is a rear view of the guitar pick holder ornament in FIG. 19.
Figure 21:
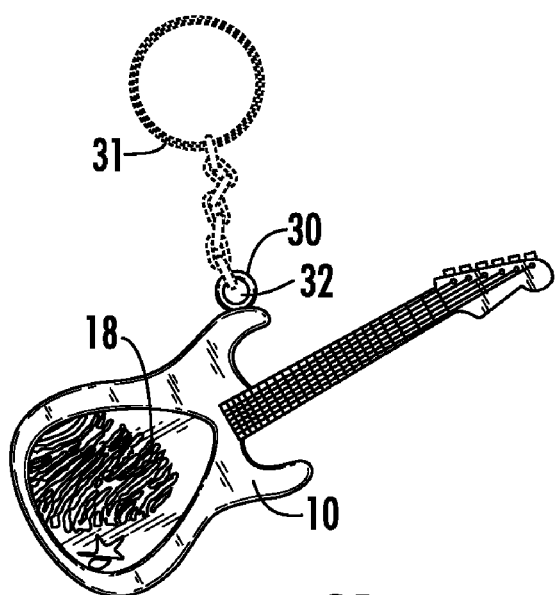
FIG. 21 is a front view of the guitar pick holder ornament in FIG. 19 with a guitar pick inserted therein.

FIGS. 1 through 3, show one embodiment of frame 10 where frame 10 is generally shaped as a guitar. Guitar pick 18 is placed and secured in the body of the guitar. Hoop 30 is placed at the end of a shortened neck of the frame 10 such that frame 10 hangs downward as a pendant. FIGS. 4 through 6 illustrate another embodiment of frame 10. Frame 10 is generally shaped as a guitar. Guitar pick 18 is placed and secured in the body of guitar. Hoop 30 is placed on a point of the body of frame 10, such that frame 10 hangs slightly off center as a pendant from ornamental material 31. Referring now to FIGS. 7 through 9, frame 10 is illustrated as having a shape configuration that is generally similar to the shape of a standard guitar pick 18. Hoop 30 is placed at the top of frame 10, such that frame 10 hangs downward as a pendant from ornamental material 31. FIGS. 10 through 12 illustrate yet another embodiment of frame 10 where frame 10 has a shape similar to the shape of a standard guitar pick 10. A plurality of gems 50, stones, glitter, or other suitable type of ornamentation adorns frame 10. Hoop 30 is placed at the top of frame 10, such that frame 10 hangs downward as a pendant from ornamental material 31. FIGS. 13 through 15 illustrate still another embodiment of frame 10 having a general shape of a heart. A plurality of gems 50, stones, glitter, or other suitable type of ornamentation adorns frame 10. Hoop 30 is placed at the top of frame 10, such that frame 10 hangs downward as a pendant from ornamental material 31. FIGS. 16 through 18 illustrate yet another embodiment of frame 10. Frame 10 is shaped similar to the shape of a standard guitar pick 10. A plurality of gems 50, stones, glitter, or other suitable type of ornamentation adorns frame 10. Hoop 30 is placed at the top of frame 10, such that frame 10 hangs downward as an earring from ornamental material 31. FIGS. 19 through 21 illustrate another embodiment of frame 10. Frame 10 is generally shaped as a guitar, wherein guitar pick 18 is placed and secured in the body of guitar. Hoop 30 is placed on a point of the body of frame 10, such that frame 10 hangs slightly off center as a keychain from ornamental material 31.

While these specific shape configurations and material choices have been illustrated in FIGS. 1 through 21 to show various guitar pick holder ornaments, it is understood that the various embodiments shown are not intended to limit this disclosure to these embodiments. FIGS. 1 through 21 are merely for exemplary purposes and are not intended to limit the invention. Any combination of embellishments 50, frame shape configurations, and ornaments types may be used with any of the embodiments included within FIGS. 1 through 21. In addition, any combination of embellishments 50, frame shape configurations, and ornaments types may be used with embodiments not shown. Frame 10 may be manufactured from any suitable material, including, but not limited to, metal, plastic, or resin. Also, while the term 'ornament' has been used throughout this disclosure, it is understood that ornament is defined as something that decorates or adorns, an accessory, an embellishment, jewelry, and/or costume jewelry.

Figure 22:
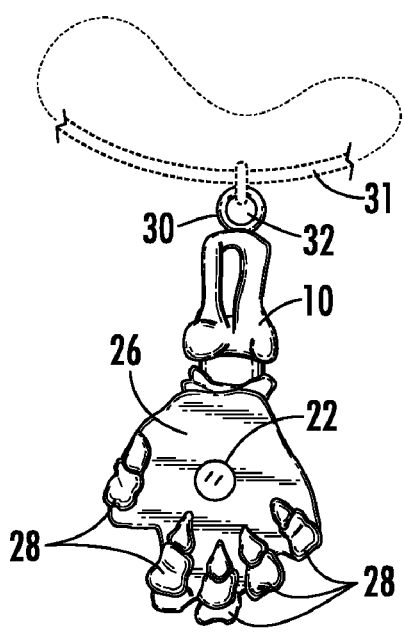
FIG. 22 is a front view of another embodiment of a guitar pick holder ornament.
Figure 23:
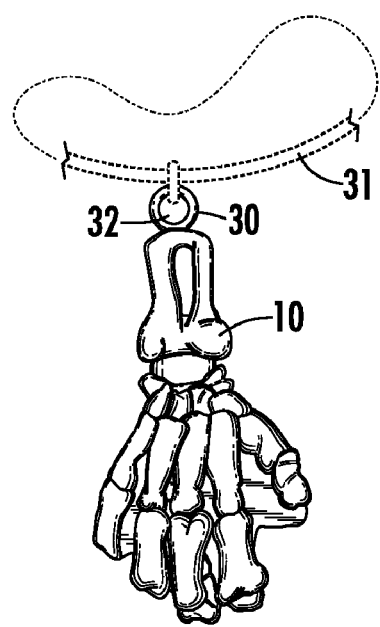
FIG. 23 is a rear view of the guitar pick holder ornament in FIG. 22.
Figure 24:
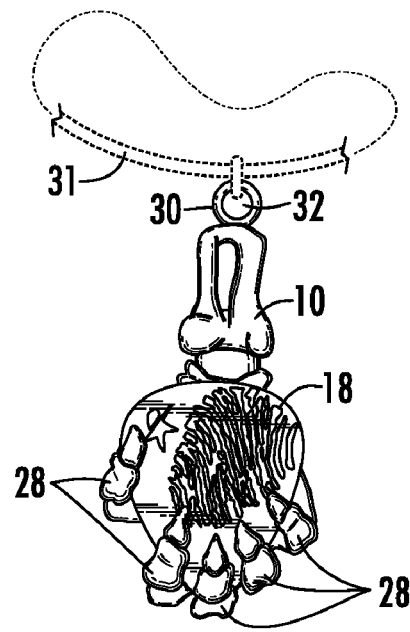
FIG. 24 is a front view of the guitar pick holder ornament in FIG. 22 with a guitar pick inserted therein.
Figure 25:
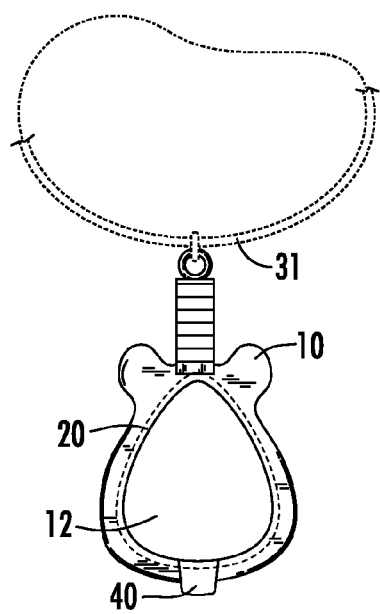
FIG. 25 is a front view of yet another embodiment of a guitar pick holder ornament.

Referring now to FIGS. 22 through 24, another embodiment includes frame 10 having a back portion 26 and a plurality of clasps 28. Clasps 28 extend from back portion 26 and curve around so that clasps are adjacent to and substantially parallel to, back portion 26. The curve of clasps 28 also creates a space for guitar pick 18 to rest on once inserted into frame 10. Clasps 28 extend substantially parallel to back portion 26 such that they extend for a portion, e.g., about one third, of the height of back portion 16. It should be noted however, that clasps 28 may extend over more or less of one third of back portion 26, so long as they serve the purpose of holding guitar pick 18 in place once it is inserted into frame 10. FIGS. 22 through 24 illustrate a plurality of clasps 28, however, as few as one clasp 28 and any number of multiple clasps 28 may be used to hold guitar pick 18 in place in frame 10. In addition, clasps 28 and back portion 26 have been described as being one piece, however, clasps 28 and back portion 26 may be two pieces, secured with an adhesive or other suitable bond, a connection, hinge, or fastening means.

Cushion 22 may be disposed on back portion 26 to press pick 18 against clasps 28 when guitar pick 18 is placed in frame 10. Guitar picks 18 are available in various thicknesses, thus frame 10 is of a thickness suitable to accommodate guitar picks 18 of different thicknesses. Cushion 22 is shown as covering only a portion of rear support plate 14, however it may cover rear support plate 14, or a larger portion of rear support plate 14. When guitar pick 18 is placed in frame 10, cushion 22 is compressed to take up any gap not filled by the dimensions of guitar pick 18.

Once guitar pick 18 is secured in frame 10, guitar pick 18 is retained until a force is applied. Guitar pick 18 does not easily move from frame 10 with basic movements or light forces from use. Guitar pick 18 is removed and inserted in frame 10 by flexing pick 18 against back portion 26. Back portion 26 may include an opening (FIG. 12) such that guitar pick 18 is visible through frame 10 when secured in frame 10.

Frame 10 also includes a hoop 30 having an aperture 32 for receiving an ornamental material 31 to create an ornament. For example, a chain of suitable gauge and length may be strung through aperture 32 to create a necklace having frame 10 as a pendant. Further, any suitable ornamental material may be used to create an ornament such as, but not limited to jewelry or costume jewelry, an earring, a bracelet, an anklet, a belly ring, a keychain, a zipper pull, a luggage tag, and/or a ring. Hoop 30 may be integral with frame 10, or hoop 30 may be secured, adhered, fastened, or otherwise connected to frame 10. Hoop 30 may also be secured to frame 10 at the top of frame 10, however hoop 30 may be secured to frame 10 at any suitable location. Frame 10 may also include a fastener (not shown) for securing frame 10 to a device such as, but not limited to a guitar, belt loop, shirt, pants, cell phone, shoe or other suitable device.

Referring now to FIGS. 25 through 28, a two-piece frame 10 includes a first half 36 and a second half 38 attached by a hinge mechanism 40. First half 36 and second half 38 have a recessed rim 20 for receiving guitar pick 18 (not shown). Guitar pick 18 (not shown) is placed in recessed rim 20 of either first half 36 or second half 38 and then first half 36 and second half 38 are closed about hinge mechanism 40, thereby securing guitar pick 18 (not shown) between first half 36 and second half 38 in recessed rim 20. Frame 10 also includes opening 12, to provide visibility to guitar pick 18 (not shown). First half 36 may include opening 12, second half 38 may include opening 12, or both first half 36 and second half 38 may include opening 12. Recessed rim 20 is generally shaped with a larger diameter than opening 12 such that guitar pick 18 (not shown) cannot pass through opening 12.

Frame 10 is shown as including a fastener 42. First half 36 includes an aperture 48 for receiving a pin 46 disposed on second half 38. Pin 46 is inserted into aperture 48 as second half 38 and first half 36 are rotated about hinge mechanism 40. Upon insertion of pin 46 into aperture 48, pin 46 is secured in aperture 48, thereby securing first half 36 to second half 38 and preventing first half 36 from separating 38 from second half 38. While pin 46 and aperture 48 are described herein, it is understood that any suitable fastener may be used to secure first half 36 and second half 38.

Figure 26:
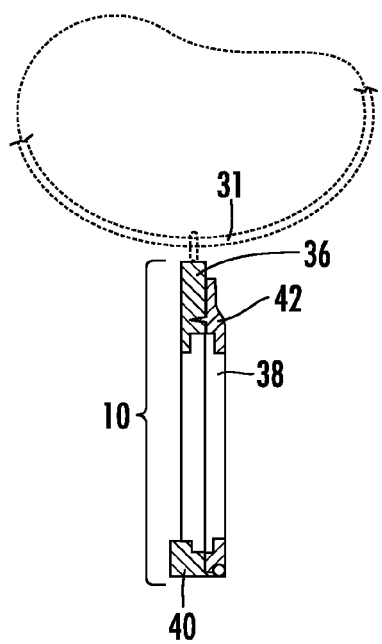
FIG. 26 is a side view of the guitar pick holder ornament in FIG. 25 in a closed position.
Figure 27:
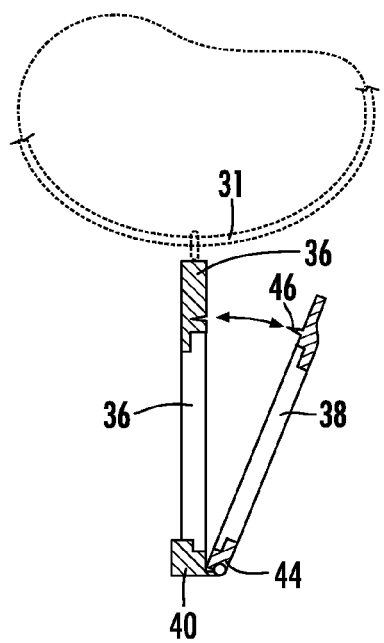
FIG. 27 is a side view of the guitar pick holder ornament in FIG. 25 in an open position.
Figure 28:
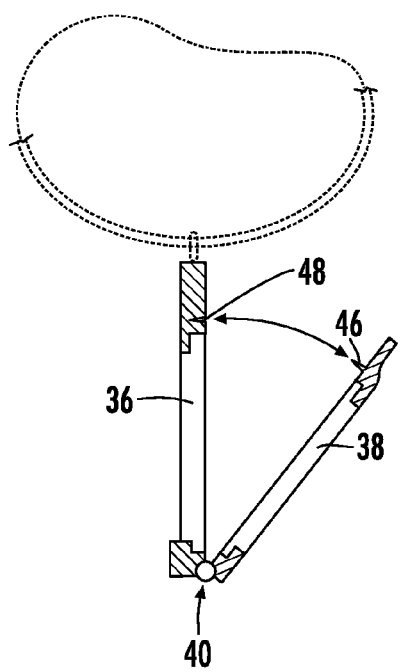
FIG. 28 is a side view of still another embodiment of a guitar pick holder ornament in an open position.

Hinge mechanism 40 is shown as being disposed at the bottom of frame 10, however hinge mechanism 40 may be disposed at any suitable location along frame 10. Hinge mechanism 40 is shown in FIGS. 26 and 27 as having two interlocking clasps 44 that are rotatable about each other. As shown in FIG. 28, another embodiment of hinge mechanism 40 is shown. Hinge mechanism 40 may be a living hinge or other suitable hinge type mechanism 40. Hinge mechanism 40 may also be any suitable type of rotatable fastening means to moveable rotate first half 36 and second half 38 from an open position to a closed position and any position between open and closed.

Figures 29, 30, 31, 32:
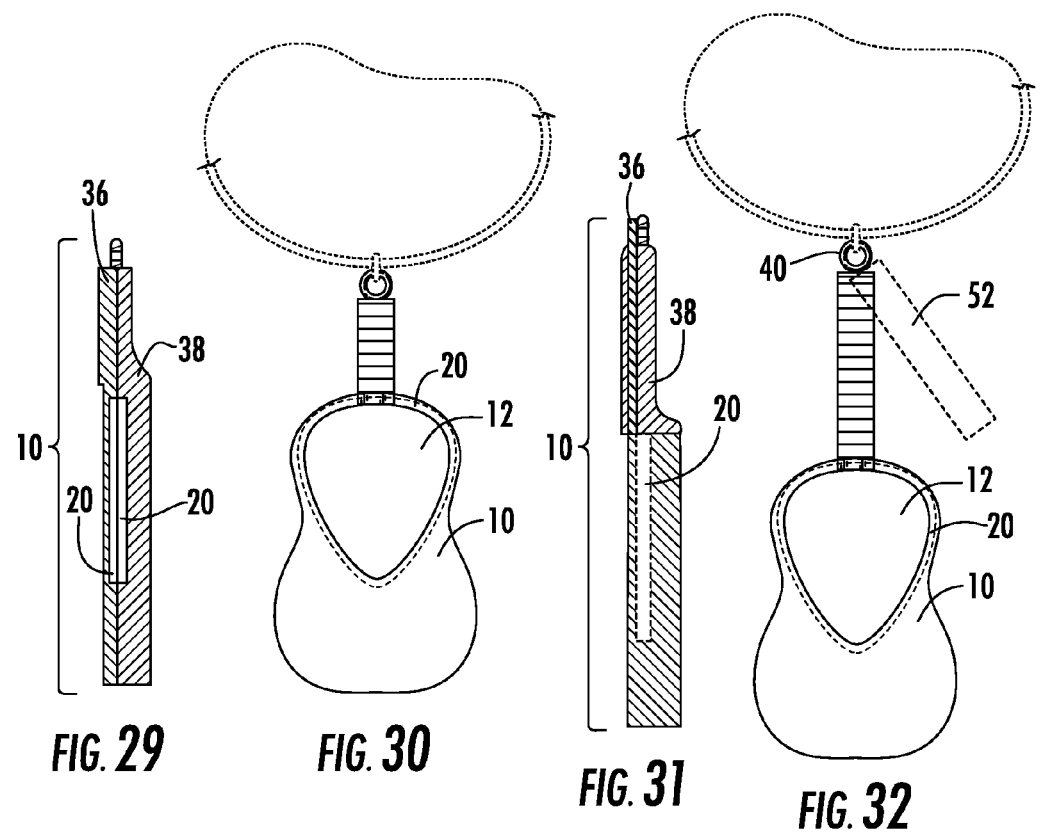
FIG. 29 is a side view of another embodiment of a guitar pick holder ornament.
FIG. 30 is a front view of the guitar pick holder ornament in FIG. 29.
FIG. 31 is a side view of yet another embodiment of a guitar pick holder ornament.
FIG. 32 is a front view of the guitar pick holder ornament in FIG. 31.

Referring now to FIGS. 29 and 30, yet another embodiment of frame 10 is shown. Frame 10 includes a mateable first half 36 and a mateable second half 38. First half 36 and second half 38 may be mateable with fastening mechanism such as, but not limited to, a magnetic connection. First half 36 and second half 38 have recessed rim 20 for receiving guitar pick 18 (not shown). Guitar pick 18 (not shown) is inserted into recessed rim 20 of either first half 36 or second half 38. Second half 38 and first half 36 are mated and secured together, securing guitar pick 18 (not shown) between first half 36 and second half 38. First half 36 and second half 38 may include opening 12 to provide visibility of one or both sides of guitar pick 18 (not shown). Opening 12 is configured with a smaller diameter than recessed rim 20 to prevent guitar pick 18 (not shown) from falling through opening 12 when placed in frame 10.

FIGS. 31 and 32 show another embodiment of frame 10 having a fastening device 52 for securing guitar pick 18 (not shown) in frame 10. Frame 10 includes recessed rim 20 configured to receive and secure guitar pick 28 (not shown). Frame also include opening for displaying guitar pick 18 (not shown) when guitar pick 18 (See FIG. 3) is secured in recessed rim. Opening 12 has a smaller diameter than recessed rim 20 to prevent guitar pick 18 (not shown) from falling through opening 12. Fastening device 52 is secured to frame 10 by hinge mechanism 40. Fastening device 52 extends below opening 12 such that fastening device 52 is partially above guitar pick 18 (not shown) and opening 12. Once guitar pick 18 (not shown) is placed in recessed rim 20, fastening device 52 is rotated about hinge mechanism 40 such that fastening device 52 secures guitar pick 18 (not shown) in recessed rim 20 in frame 10.

Figure 33:
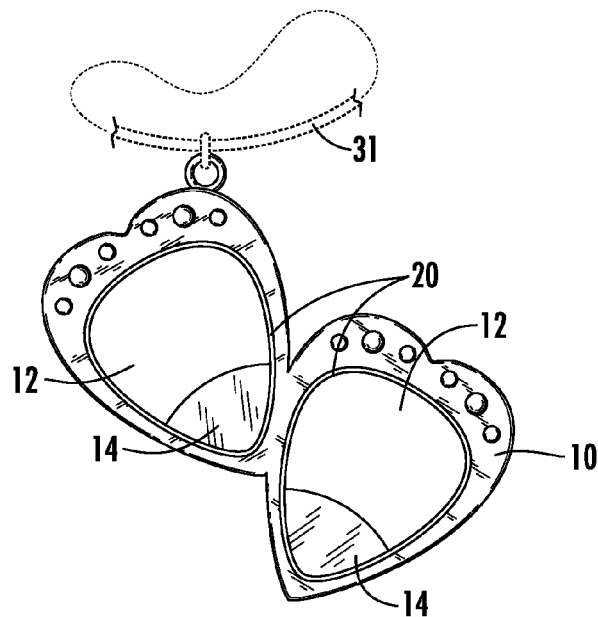
FIG. 33 is a front view still another embodiment of a guitar pick holder ornament.

As shown in FIG. 33, frame 10 may also include two openings 12, two recessed rims 20, and two rear support plates 14. Openings 12 may be side-by-side, one on top of the other, diagonally spaced or in any suitable configuration. Each recessed rim 20 is configured to receive a separate guitar pick 18, such that two guitar picks 18 are secured in frame 10 and both sides of guitar picks 18 are visible through openings 12. In addition, each opening 12 may be capable of receiving and securing multiple guitar picks 18, such that multiple guitar picks 18 may be placed in each opening 12

Frame 10 may have a depth suitable to house a recessed rim 20 with a depth suitable to receive multiple guitar picks 18 at once. For example, instead of having one guitar pick 18 secured in frame, multiple guitar picks 18 may be inserted and secured in frame, such as four guitar picks 18. The first guitar pick would be visible through opening 12 on one side of frame 10 and the fourth guitar pick 18 would be visible through opening 12 on the opposite side of frame 10. It is understood that while four guitar picks 18 have been used as an example, any number of multiple guitar picks 18 may be used. It is also understood that while guitar pick 18 has been referenced throughout the specification, any suitable object may be secured in frame 10. The term object may include, but is not limited to items of any suitable shape, configuration or size, for example, a medallion, a poker chip, a symbol, a trinket, sports memorabilia, entertainment memorabilia, memorabilia, collectibles, a golf ball marker, coins, sporting instruments, keepsake, and/or keys.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A guitar pick holder comprising:
    a frame having at least two recessed rims, the recessed rims configured to receive at least two guitar picks; and
    at least two support plates secured to the frame;
    wherein the at least two guitar picks are placed in the at least two recessed rims; and
    wherein the at least two support plates secure the at least two guitar picks in the at least two recessed rims of the frame.

2. The guitar pick holder of claim 1, wherein the frame comprises an opening, and wherein at least one guitar pick of the at least one guitar picks is visible through the opening when the at least one guitar pick is secured in the recessed rim of the frame.

3. The guitar pick holder of claim 1, wherein the frame comprises an aperture for receiving an ornamental material, and wherein when the ornamental material is placed through the aperture, the guitar pick holder is an ornament.

4. The guitar pick holder of claim 1, comprising:
    a cushion disposed on the support plate;
    wherein the cushion compresses when at least one guitar pick is placed in the frame.

5. The guitar pick holder of claim 1, comprising a fastener extending from the frame, the fastener configured to secure the guitar pick holder to a device.

6. A guitar pick holder comprising:
    a frame comprising:
        a first half having a recessed rim, the recessed rim configured to receive a guitar pick; and
        a second half having a recessed rim, the recessed rim configured to receive a guitar pick, the second frame configured to attach to the first frame in at least an open position and a closed position;
    wherein the guitar pick is secured in the guitar pick holder when the first frame and second frame are in the closed position.

7. The guitar pick holder of claim 6, comprising a fastener configured to secure the first half to the second half in the closed position.

8. The guitar pick holder of claim 6, wherein at least one of the first half and the second half comprise an opening, wherein at least one guitar pick is placed between the first half and the second half, and wherein at least one guitar pick of the at least one guitar pick is visible through the opening.

9. The guitar pick holder of claim 6, wherein the frame comprises an hoop having an aperture for receiving an ornamental material, and wherein when the ornamental material is placed through the aperture, the guitar pick holder is an ornament.

10. The guitar pick holder of claim 6, wherein the frame comprises a second fastener for securing the guitar pick to a device.

11. The guitar pick holder of claim 7, wherein the fastener is a clasp.

12. The guitar pick holder of claim 7, wherein the fastener is a magnet.

13. The guitar pick holder of claim 6, wherein the first frame and the second frame are hingedly attached and rotatable about a hinge.

14. The guitar pick holder of claim 6, wherein the recessed rim is configured to receive at least two guitar picks.

15. The guitar pick holder of claim 6, comprising:
a frame comprising:
 a first half having at least two recessed rims, the at least two recessed rims configured to receive at least two guitar picks; and
 a second half having at least two recessed rims the at least two recessed rims configured to receive at least two guitar picks, the second frame configured to attach to the first frame in at least an open position and a closed position;
wherein the at least two guitar picks are secured in the guitar pick holder when the first frame and second frame are in the closed position.

* * * * *